(12) United States Patent
Malkowski et al.

(10) Patent No.: US 9,693,760 B2
(45) Date of Patent: Jul. 4, 2017

(54) TRIANGULATION METHODS WITH HOLLOW SEGMENTS

(71) Applicant: Covidien LP, Mansfield, MA (US)

(72) Inventors: Jaroslaw T. Malkowski, Trumbull, CT (US); Eric Taylor, East Hampton, CT (US); Peter Hathaway, Lebanon, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/986,755

(22) Filed: Jan. 4, 2016

(65) Prior Publication Data

US 2016/0113638 A1 Apr. 28, 2016

Related U.S. Application Data

(62) Division of application No. 13/735,073, filed on Jan. 7, 2013, now Pat. No. 9,226,741.

(60) Provisional application No. 61/584,732, filed on Jan. 9, 2012.

(51) Int. Cl.
| | |
|---|---|
| *A61B 1/32* | (2006.01) |
| *A61B 17/00* | (2006.01) |
| *A61B 17/02* | (2006.01) |
| *A61B 17/34* | (2006.01) |
| *A61B 90/50* | (2016.01) |
| *A61B 17/29* | (2006.01) |
| *A61B 90/00* | (2016.01) |

(52) U.S. Cl.
CPC .... *A61B 17/00234* (2013.01); *A61B 17/0218* (2013.01); *A61B 17/0293* (2013.01); *A61B 17/3423* (2013.01); *A61B 90/50* (2016.02); *A61B 2017/003* (2013.01); *A61B 2017/00323* (2013.01); *A61B 2017/2906* (2013.01); *A61B 2017/2908* (2013.01); *A61B 2017/3443* (2013.01); *A61B 2017/3447* (2013.01); *A61B 2090/0811* (2016.02)

(58) Field of Classification Search
CPC . A61B 1/0052–1/0057; A61B 17/3415; A61B 17/3417
USPC ............... 600/101, 564, 204–207, 102, 104, 600/139–142, 114–115; 604/19, 523, 528
See application file for complete search history.

(56) References Cited

U.S. PATENT DOCUMENTS

| | | | | |
|---|---|---|---|---|
| 5,386,818 A | * | 2/1995 | Schneebaum | A61B 1/018 600/104 |
| 5,549,637 A | * | 8/1996 | Crainich | A61B 17/29 606/170 |
| 5,603,723 A | * | 2/1997 | Aranyi | A61B 17/29 606/174 |

(Continued)

FOREIGN PATENT DOCUMENTS

WO 02/07611 1/2002

*Primary Examiner* — Eduardo C Robert
*Assistant Examiner* — Michelle C Eckman

(57) ABSTRACT

A surgical apparatus providing access to an underlying body cavity through a tissue tract articulates a flexible surgical object inserted therein. The surgical apparatus includes a tube member defining a longitudinal axis and a lumen therethrough to receive the flexible surgical object. The tube member includes a proximal member, a middle member connected to the proximal member at a first joint, and a distal member connected to the middle member at a second joint. The surgical apparatus also includes articulation mechanisms to articulate the tube member.

10 Claims, 9 Drawing Sheets

(56) References Cited

U.S. PATENT DOCUMENTS

| | | | |
|---|---|---|---|
| 5,609,565 A | 3/1997 | Nakamura | |
| 5,743,456 A * | 4/1998 | Jones | A61B 17/0684 227/176.1 |
| 5,860,995 A * | 1/1999 | Berkelaar | A61B 17/29 606/174 |
| 5,899,425 A | 5/1999 | Corey, Jr. et al. | |
| 5,931,832 A * | 8/1999 | Jensen | B25J 9/1065 128/898 |
| 6,248,062 B1 * | 6/2001 | Adler | A61B 17/0218 600/204 |
| 6,632,170 B1 | 10/2003 | Bohanan et al. | |
| 6,705,989 B2 * | 3/2004 | Cuschieri | A61B 17/0218 600/208 |
| 7,250,027 B2 * | 7/2007 | Barry | A61B 1/0056 600/139 |
| 7,615,066 B2 * | 11/2009 | Danitz | A61B 1/0055 600/139 |
| 7,637,905 B2 * | 12/2009 | Saadat | A61B 1/0055 600/104 |
| 7,682,319 B2 * | 3/2010 | Martin | A61B 50/30 600/139 |
| 7,850,600 B1 * | 12/2010 | Piskun | A61B 1/05 600/114 |
| 7,976,559 B2 | 7/2011 | Goldfarb et al. | |
| 8,439,828 B2 * | 5/2013 | Dejima | A61B 1/0052 600/104 |
| 8,517,933 B2 | 8/2013 | Mohr | |
| 8,550,989 B2 * | 10/2013 | Dohi | A61B 1/00078 600/114 |
| 8,562,592 B2 | 10/2013 | Conlon et al. | |
| 8,657,736 B2 * | 2/2014 | Diolaiti | A61B 19/20 318/568.25 |
| 8,764,765 B2 | 7/2014 | Piskun et al. | |
| 8,771,180 B2 | 7/2014 | Mohr | |
| 8,821,388 B2 * | 9/2014 | Naito | A61B 1/0055 600/141 |
| 9,226,741 B2 | 1/2016 | Malkowski et al. | |
| 2003/0036748 A1 * | 2/2003 | Cooper | A61B 17/00234 606/1 |
| 2003/0236549 A1 * | 12/2003 | Bonadio | A61B 17/29 606/205 |
| 2005/0165272 A1 * | 7/2005 | Okada | A61B 1/0008 600/114 |
| 2005/0272977 A1 * | 12/2005 | Saadat | A61B 1/0008 600/114 |
| 2006/0020241 A1 * | 1/2006 | Piskun | A61B 17/3421 604/93.01 |
| 2006/0041188 A1 * | 2/2006 | Dirusso | A61B 1/0055 600/146 |
| 2006/0094932 A1 * | 5/2006 | Goldfarb | A61B 17/02 600/229 |
| 2006/0094933 A1 | 5/2006 | Goldfarb et al. | |
| 2006/0178560 A1 * | 8/2006 | Saadat | A61B 1/0055 600/114 |
| 2006/0199999 A1 * | 9/2006 | Ikeda | A61B 1/0052 600/141 |
| 2007/0049966 A1 * | 3/2007 | Bonadio | A61B 17/00234 606/206 |
| 2007/0244358 A1 * | 10/2007 | Lee | A61B 17/00234 600/114 |
| 2007/0260114 A1 * | 11/2007 | Miyamoto | A61B 17/29 600/114 |
| 2007/0270679 A1 | 11/2007 | Nguyen et al. | |
| 2007/0276430 A1 * | 11/2007 | Lee | A61B 1/00071 606/205 |
| 2007/0287889 A1 * | 12/2007 | Mohr | A61B 1/00082 600/207 |
| 2008/0051629 A1 * | 2/2008 | Sugiyama | A61B 1/00193 600/114 |
| 2008/0051631 A1 * | 2/2008 | Dejima | A61B 1/0052 600/114 |
| 2008/0064927 A1 | 3/2008 | Larkin et al. | |
| 2008/0065098 A1 * | 3/2008 | Larkin | A61B 1/00087 606/130 |
| 2008/0065107 A1 | 3/2008 | Larkin et al. | |
| 2008/0119871 A1 * | 5/2008 | Brock | A61B 34/20 606/130 |
| 2008/0214893 A1 * | 9/2008 | Tartaglia | A61B 1/00147 600/114 |
| 2009/0043299 A1 | 2/2009 | Racz | |
| 2009/0062606 A1 * | 3/2009 | Ueda | A61B 1/00154 600/114 |
| 2009/0093752 A1 | 4/2009 | Richard et al. | |
| 2009/0209819 A1 * | 8/2009 | Kitagawa | A61B 1/0055 600/142 |
| 2010/0004509 A1 * | 1/2010 | Naito | A61B 1/0055 600/141 |
| 2010/0016659 A1 * | 1/2010 | Weitzner | A61B 1/00073 600/104 |
| 2010/0030018 A1 * | 2/2010 | Fortier | A61B 17/29 600/104 |
| 2010/0057121 A1 * | 3/2010 | Piskun | A61B 17/29 606/206 |
| 2010/0185053 A1 * | 7/2010 | Hagen | A61B 1/00154 600/114 |
| 2010/0298824 A1 * | 11/2010 | Rothstein | A61B 18/1445 606/41 |
| 2011/0087269 A1 * | 4/2011 | Stokes | A61B 17/29 606/206 |
| 2011/0105843 A1 * | 5/2011 | Mueller | A61B 17/29 600/114 |
| 2011/0178370 A1 * | 7/2011 | Frassica | A61B 90/361 600/114 |
| 2011/0184459 A1 * | 7/2011 | Malkowski | A61B 17/29 606/206 |
| 2011/0275901 A1 * | 11/2011 | Shelton, IV | A61B 17/29 600/204 |
| 2011/0276057 A1 * | 11/2011 | Conlon | A61B 17/29 606/130 |
| 2011/0282149 A1 * | 11/2011 | Vargas | A61M 25/0021 600/114 |
| 2011/0295065 A1 * | 12/2011 | Gurusamy | A61B 1/008 600/114 |
| 2012/0022334 A1 | 1/2012 | Piskun | |
| 2012/0133752 A1 * | 5/2012 | Bry | A61B 8/4227 348/65 |
| 2012/0220830 A1 * | 8/2012 | Yang | A61B 1/008 600/137 |
| 2012/0253116 A1 * | 10/2012 | Sniffin | A61B 18/14 600/106 |
| 2012/0253131 A1 * | 10/2012 | Malkowski | A61B 17/3421 600/201 |
| 2012/0253132 A1 * | 10/2012 | Davis | A61B 17/3423 600/201 |
| 2012/0253327 A1 * | 10/2012 | Malkowski | A61B 17/3423 606/1 |
| 2012/0296169 A1 * | 11/2012 | Kleyman | A61B 1/3132 600/204 |
| 2013/0012929 A1 * | 1/2013 | Malkowski | A61B 17/29 606/1 |
| 2013/0131450 A1 * | 5/2013 | Surti | A61B 1/00135 600/114 |
| 2013/0178708 A1 * | 7/2013 | Malkowski | A61B 17/0293 600/204 |
| 2013/0178712 A1 * | 7/2013 | Malkowski | A61B 17/0293 600/208 |
| 2013/0178837 A1 * | 7/2013 | Malkowski | A61B 17/0293 606/1 |
| 2013/0317306 A1 | 11/2013 | Mohr | |
| 2013/0317309 A1 | 11/2013 | Mohr | |
| 2013/0345511 A1 * | 12/2013 | Piskun | A61B 17/0218 600/114 |
| 2014/0051930 A1 * | 2/2014 | Drochner | A61B 17/0218 600/203 |
| 2014/0088361 A1 * | 3/2014 | Hrayr | A61B 1/00183 600/111 |
| 2014/0163326 A1 * | 6/2014 | Forsell | A61B 17/3423 600/207 |

(56) References Cited

U.S. PATENT DOCUMENTS

| | | | |
|---|---|---|---|
| 2014/0221750 A1 | 8/2014 | Weitzner | |
| 2014/0243868 A1* | 8/2014 | Parihar | A61B 17/00234 606/185 |
| 2014/0249544 A1 | 9/2014 | Diolaiti | |
| 2014/0316432 A1* | 10/2014 | Malkowski | A61B 17/00234 606/130 |
| 2014/0323809 A1* | 10/2014 | Bonadio | A61B 17/3421 600/205 |

* cited by examiner

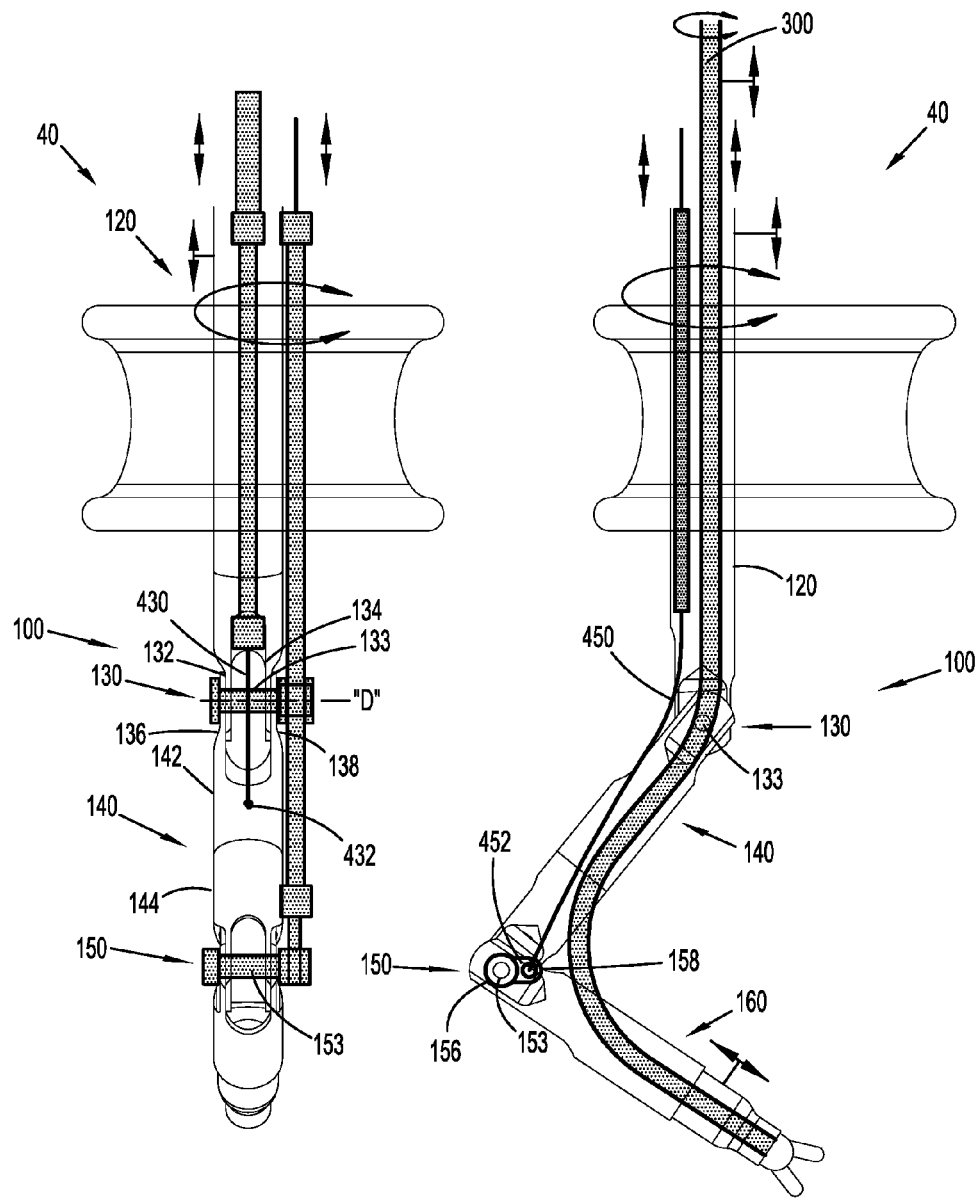
FIG. 4A  FIG. 4B
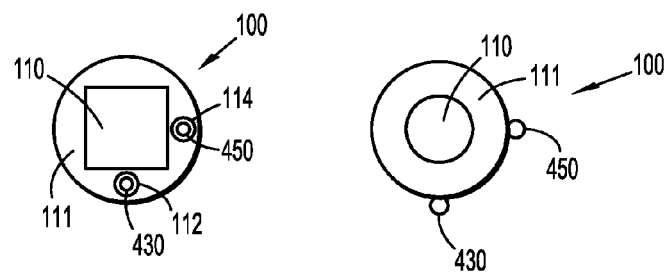
FIG. 5A  FIG. 5B

TRIANGULATION METHODS WITH HOLLOW SEGMENTS

CROSS-REFERENCE TO RELATED APPLICATIONS

This application is a divisional application of U.S. patent application Ser. No. 13/735,073, filed Jan. 7, 2013, which claims the benefit of and priority to U.S. Provisional Patent Application No. 61/584,732, filed Jan. 9, 2012, the entire disclosures of each of which are incorporated by reference herein.

BACKGROUND

1. Technical Field

The present disclosure relates generally to surgical instruments for use with a seal anchor member. More particularly, the present disclosure relates to articulating surgical instruments usable with a seal anchor member that provides multiple instrument access through a single opening in a minimally invasive surgical procedure.

2. Description of Related Art

Increasingly, many surgical procedures are performed through small openings in the skin. As compared to the larger openings typically required in traditional procedures, smaller openings result in less trauma to the patient. By reducing the trauma to the patient, the time required for recovery is also reduced. Generally, the surgical procedures that are performed through small openings in the skin are referred to as endoscopic. If the procedure is performed on the patient's abdomen, the procedure is referred to as laparoscopic. Throughout the present disclosure, the term minimally invasive is to be understood as encompassing both endoscopic and laparoscopic procedures.

During a typical minimally invasive procedure, surgical objects, such as surgical access devices (e.g., trocar and cannula assemblies) or endoscopes, are inserted into the patient's body through the opening in tissue. In general, prior to the introduction of the surgical object into the patient's body, insufflation gas is used to enlarge the area surrounding the target surgical site to create a larger, more accessible work area. Accordingly, the maintenance of a substantially fluid-tight seal is desirable so as to inhibit the escape of the insufflation gas and the deflation or collapse of the enlarged surgical site. In response to this, various access devices with sealing features are used during the course of minimally invasive procedures to provide an access for surgical objects to enter the patient's body. Each of these devices is configured for use through a single opening or a naturally occurring orifice (i.e. mouth, anus, or vagina) while allowing multiple instruments to be inserted through the device to access the working space beyond the device.

During procedures employing multiple surgical instruments through a single opening access device, it is advantageous to articulate the surgical instruments, especially the end effectors of the surgical instruments, to improve coordination among the surgical instruments.

Access devices in the prior art do not have well-defined articulation mechanisms in place to articulate the surgical instruments inserted therethrough, limiting the use of the surgical instruments and the access devices to a few limited surgical procedures.

Accordingly, a continuing need exists for a surgical apparatus with articulation features that facilitate articulation of surgical instruments inserted through an access device.

SUMMARY

The present disclosure features a surgical apparatus for articulating a flexible surgical object to access an underlying body cavity through a tissue tract. The surgical apparatus includes a tube member which defines a longitudinal axis and a lumen therethrough to receive the flexible surgical object therein. The tube member includes a proximal member, a middle member jointly connected to the proximal member at a first joint, and a distal member jointly connected to the middle member at a second joint.

The tube member is configured to be inserted through an access device. The access device is configured to be positioned within the tissue tract for providing access to the underlying body cavity.

The first joint and the second joint may have a first, parallel configuration in which their axes are in a parallel relation. Additionally, the first joint and the second joint may have a second, perpendicular configuration in which their axes are generally perpendicular to each other.

The middle member may include a first segment and a second segment disposed axially along the middle member. In one embodiment, the first and second segments of the middle member are fused together. In another embodiment, the first and second segments of the middle member are configured to rotate relative to each other to transit the first and second joints from the first, parallel configuration to the second, perpendicular configuration.

The distal member may include a first segment and a second segment disposed axially along the distal member. The distal member may define a retracted position in which the second segment is retracted within the first segment. The distal member may also define an extended position in which the second segment is extended outside of the first segment. Further, the distal member is dimensioned to permit rotation of an end effector of the flexible surgical object therein.

In one embodiment, the surgical apparatus may include at least one cable associated with at least one of the first and second joints in a manner such that longitudinal motion of the at least one cable causes rotation of the associated joint. The at least one cable may be associated with the first joint such that longitudinal motion of the cable translates into pivotal motion of the middle member relative to the proximal member. The at least one cable may be associated with the second joint such that longitudinal motion of the at least one cable translates into pivotal motion of the distal member relative to the middle member.

In another embodiment, the surgical apparatus may include a rigid arm extending along the tube member. The rigid arm is hingedly connected to a sleeve which is mounted about the distal member. Longitudinal motion of the rigid arm articulates the middle member and the distal member relative to the proximal member.

In yet another embodiment, the surgical apparatus may include a closed-loop system to effect rotation of at least one of the first and second joints. The closed-loop system includes a rotatable member disposed proximally beyond the tube member and a cable looping around the rotatable member and one of the first and second joints.

In another embodiment, the surgical apparatus may include a rotation system to effect relative rotation between the first and second segments of the middle member. The rotation system may include a torque shaft.

Also disclosed herein is a method of articulating a flexible surgical instrument positioned within a tissue tract accessing an underlying body cavity. The method includes positioning a surgical apparatus within the tissue tract. The surgical apparatus includes a tube member defining a longitudinal axis and a lumen therethrough to receive the flexible surgical object therein. The tube member includes a proximal member, a middle member connected to the proximal member at a first joint, and a distal member connected to the middle member at a second joint.

The method also includes inserting the tube member into an access device, which is configured to be positioned within the tissue tract for providing access to the underlying body cavity. The method further includes inserting the flexible surgical instrument into the tube member, and articulating the tube member to articulate the flexible surgical instrument.

In one embodiment, the surgical apparatus includes at least one cable associated with at least one of the first and second joints in a manner such that pulling the at least one cable rotates the associated joint.

In another embodiment, the surgical apparatus includes a rigid arm extending along the tube member, and a sleeve mounted about the distal member, the rigid arm and the sleeve being hingedly connected to each other. In this embodiment, the method includes pulling the rigid arm to articulate the middle member and the distal member relative to the proximal member.

In yet another embodiment, the surgical apparatus includes a closed-loop system which effects rotation of at least one of the first and second joints.

In yet another alternate embodiment, the surgical apparatus includes a rotation system which effects relative rotation between a first segment and a second segment that are disposed axially along the middle member.

DESCRIPTION OF THE DRAWINGS

The above and other aspects, features, and advantages of the present disclosure will become more apparent in light of the following detailed description when taken in conjunction with the accompanying drawings in which:

FIGS. 4A-B illustrate one embodiment of the surgical apparatus of FIG. 1 including a single cable associated with each joint;

FIG. 5A is a schematic cross-sectional view of the surgical apparatus of FIG. 1 taken along the line "5-5" of FIG. 1;

FIG. 5B is an alternate schematic cross-sectional view of the surgical apparatus of FIG. 1 taken along the line "5-5" of FIG. 1;

DETAILED DESCRIPTION

Figure 1:
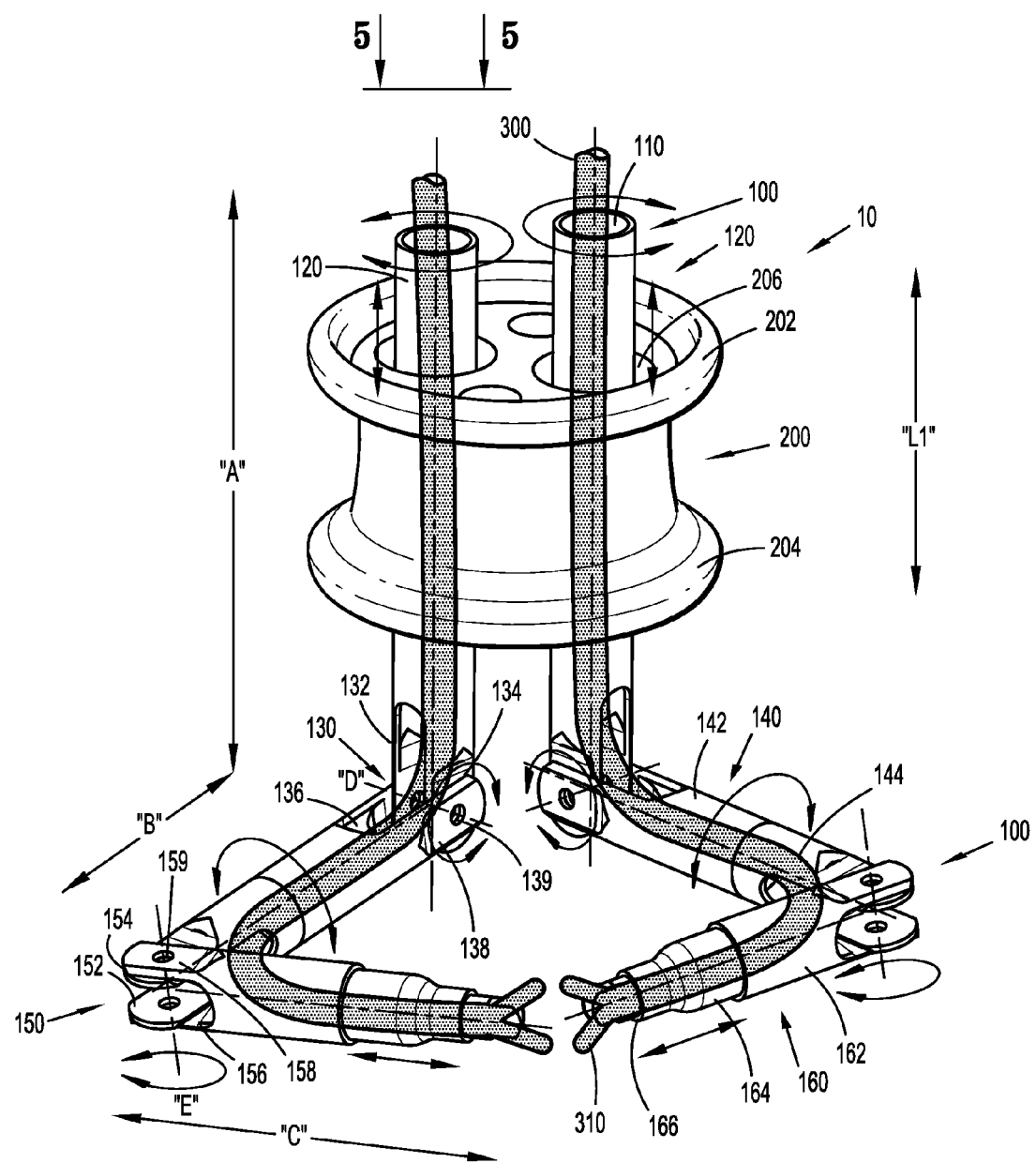
FIG. 1 is a front perspective view of a surgical apparatus in accordance with the principles of the present disclosure illustrating tube members positioned through an anchor member with surgical objects disposed therein.

The present invention describes a surgical apparatus and methods of articulating a flexible surgical object to access an underlying body cavity with the use of a tube member.

Particular embodiments of the present disclosure will be described herein with reference to the accompanying drawings. As shown in the drawings and as described throughout the following description, and as is traditional when referring to relative positioning on an object, the term "proximal" or "trailing" refers to the end of the apparatus that is closer to the user and the term "distal" or "leading" refers to the end of the apparatus that is farther from the user. In the following description, well-known functions or constructions are not described in detail to avoid obscuring the present disclosure in unnecessary detail.

Referring now to the drawings, in which like reference numerals identify identical or substantially similar parts throughout the several views, FIG. 1 illustrates an apparatus 10 including at least one tube member 100 configured to be positioned through an anchor member 200.

The anchor member 200 is a device used in minimal invasive surgery which facilitates multiple instrument access through a single opening, e.g., through the abdominal or peritoneal lining, or a naturally occurring orifice (i.e. mouth, anus, or vagina). An example of such an anchor member is disclosed in U.S. patent application Ser. No. 12/244,024, US Pub. No. 2009/0093752 A1, filed Oct. 2, 2008, the entire contents of which are hereby incorporated by reference herein.

As illustrated in FIG. 1, the anchor member 200 defines a proximal end 202, a distal end 204, and a plurality of longitudinal ports 206 extending between the proximal end 202 and the distal end 204, such as four longitudinal ports 206 shown in FIG. 1. The longitudinal ports 206 may have uniform dimensions or different dimensions. It is envisioned that at least one longitudinal port 206 is dimensioned to receive a tube member 100.

The anchor member 200 has a longitudinal length "L1," greater than or equal to the minimum length required to anchor the surgical apparatus 10 within any type of tissue tract. The anchor member 200 may define a generally cylindrical configuration. However, it is contemplated that the anchor member 200 may define other configurations both prior and subsequent to insertion within the tissue tract.

The anchor member 200 may be made from a semi-resilient, disposable, compressible, and flexible type material, for example, but not limited to, a suitable foam, gel material, or soft rubber having sufficient compliance to establish a sealing relation with the tissue tract. In one embodiment, the foam includes a polyisoprene material.

Figure 6:
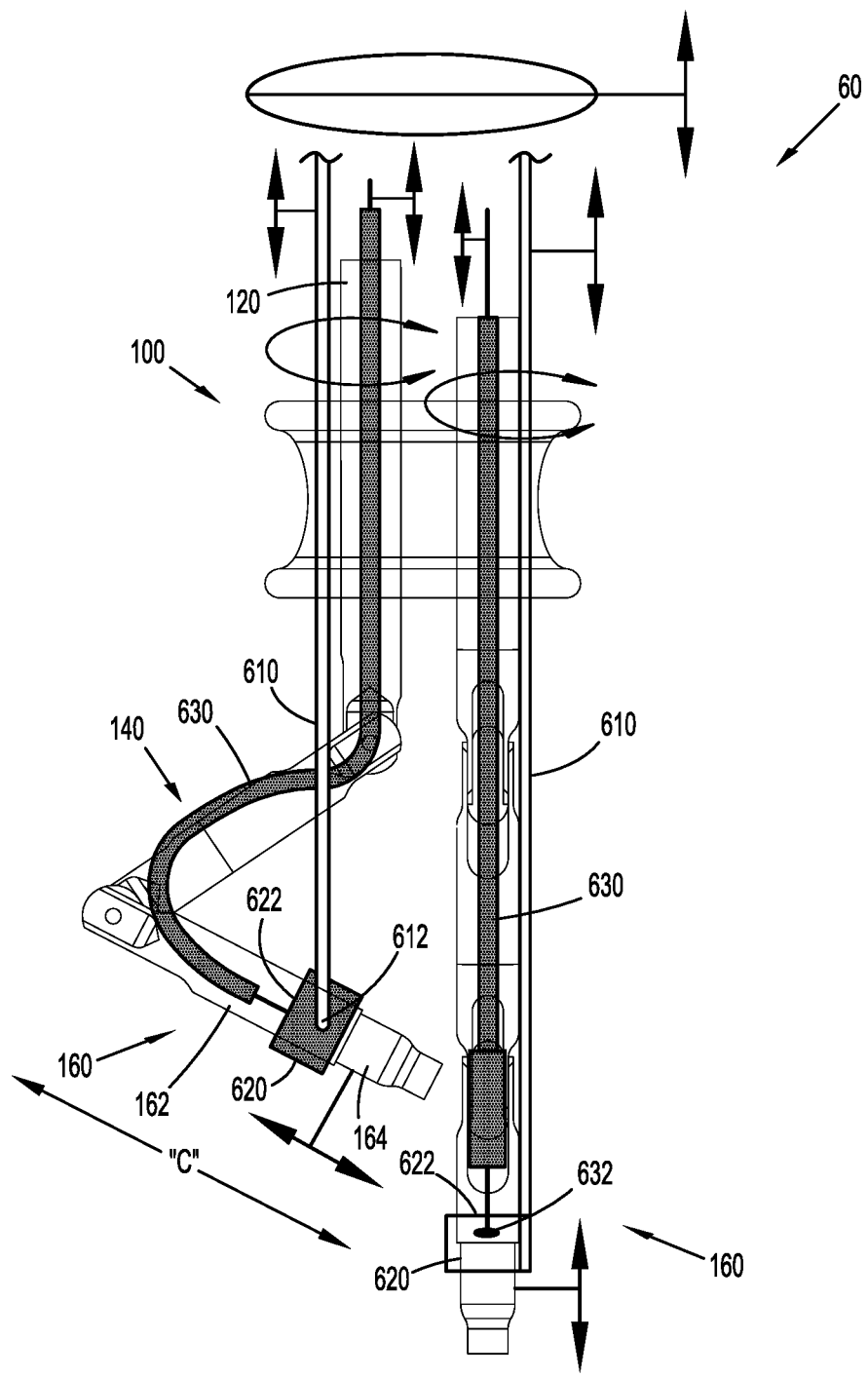
FIG. 6 illustrates another embodiment of the surgical apparatus of FIG. 1 including a rigid member and a sleeve connected thereto with the rigid member disposed outside of the tube member.
Figure 7:
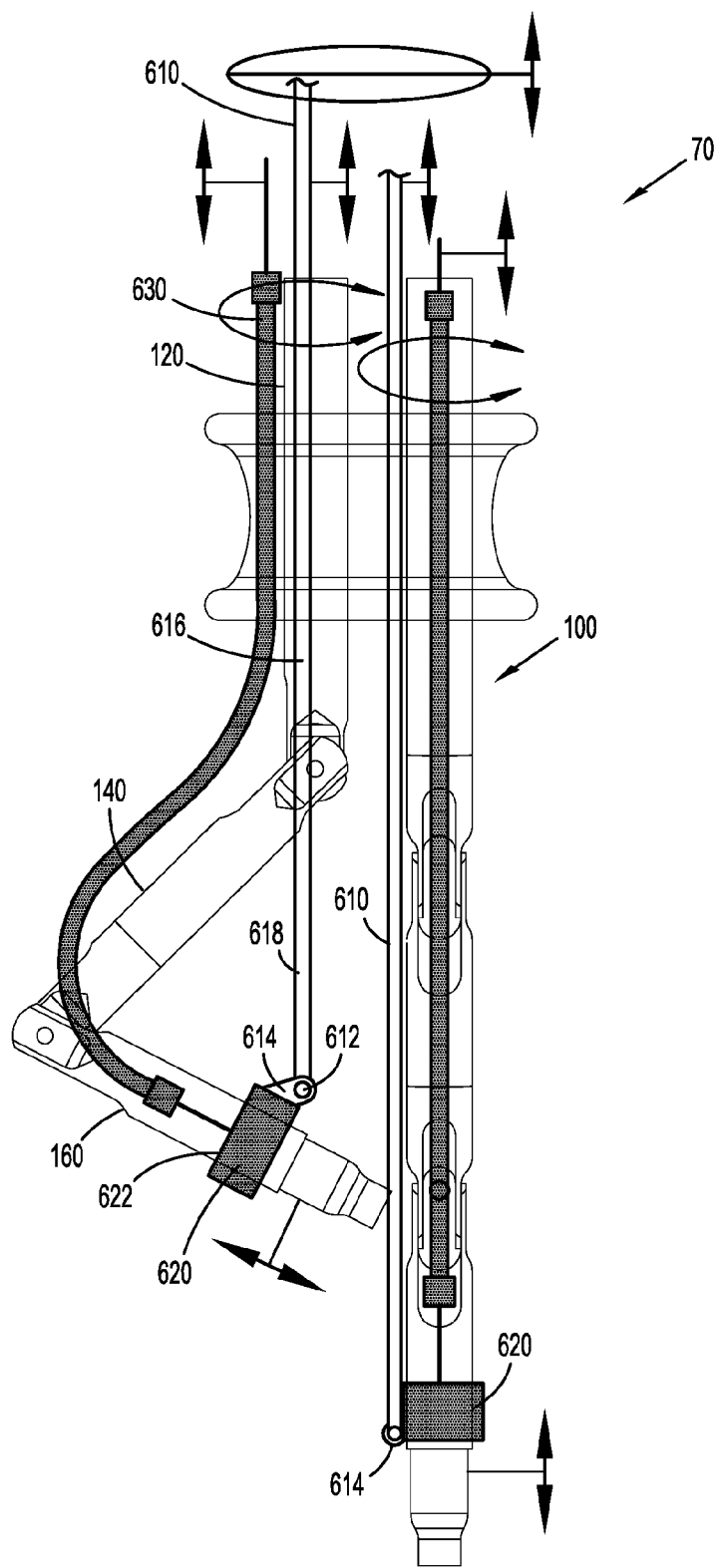
FIG. 7 illustrates an alternate embodiment of the surgical apparatus of FIG. 6 with the rigid member disposed partially within the tube member.

The tube member 100 defines a linear configuration, e.g. as shown in FIGS. 6 and 7, in which the tube member 100 as a whole exhibits a generally cylindrical shape extending axially in a single dimension. The tube member 100 can be articulated to other configurations, e.g., as illustrated in FIG. 1.

As illustrated in FIG. 1, the tube member 100 defines a lumen 110 therein along its length, configured to receive a surgical object 300 therein. The surgical object 300 could be any surgical instrument such as endoscope, grasper, stapler, forceps or the like. The surgical object 300 includes a flexible material that will conform to various configurations of the tube member 100.

FIGS. 5A-B illustrate cross-sectional views of the tube member 100. In one embodiment, as illustrated in FIG. 5A, the tube member 100 defines an inner wall 111 which exhibits a square-shaped profile. Alternatively, as shown in FIG. 5B, the inner wall 11 exhibits a circular-shaped profile.

With reference to FIG. 1, the tube member 100 includes a proximal member 120, a middle member 140 and a distal member 160 extending along the axes "A", "B" and "C," respectively. The proximal member 120 and the middle member 140 are connected at a first joint 130. The middle member 140 and the distal member 160 are connected at a second joint 150. Each member 120, 140 and 160 may define a generally cylindrical or hollow configuration. The lumen 110 of the tube member 100 extends through all three members 120, 140 and 160. When the tube member 100 is in the linear configuration, all three members 120, 140 and 160 are coaxially aligned with respect to each other, extending in a single dimension, as shown in FIGS. 6 and 7. When the tube member 100 is in the articulated configuration, each member 120, 140, 160 may extend in a different dimension, as shown in FIG. 1. Detailed description of each member is provided below.

The proximal member 120 is rotatable about the longitudinal axis "A," as illustrated in FIG. 1. Rotation of the proximal member 120 causes the tube member 100 as a whole to rotate about the longitudinal axis "A." The proximal member 120 may also move longitudinally in a proximal or distal direction along the longitudinal axis "A", e.g., as the tube member 100 advances into or withdraws from the anchor member 200. In one embodiment, the proximal member 120 is a hollow segment that allows the surgical object 300 to pass therethrough.

Figure 2:
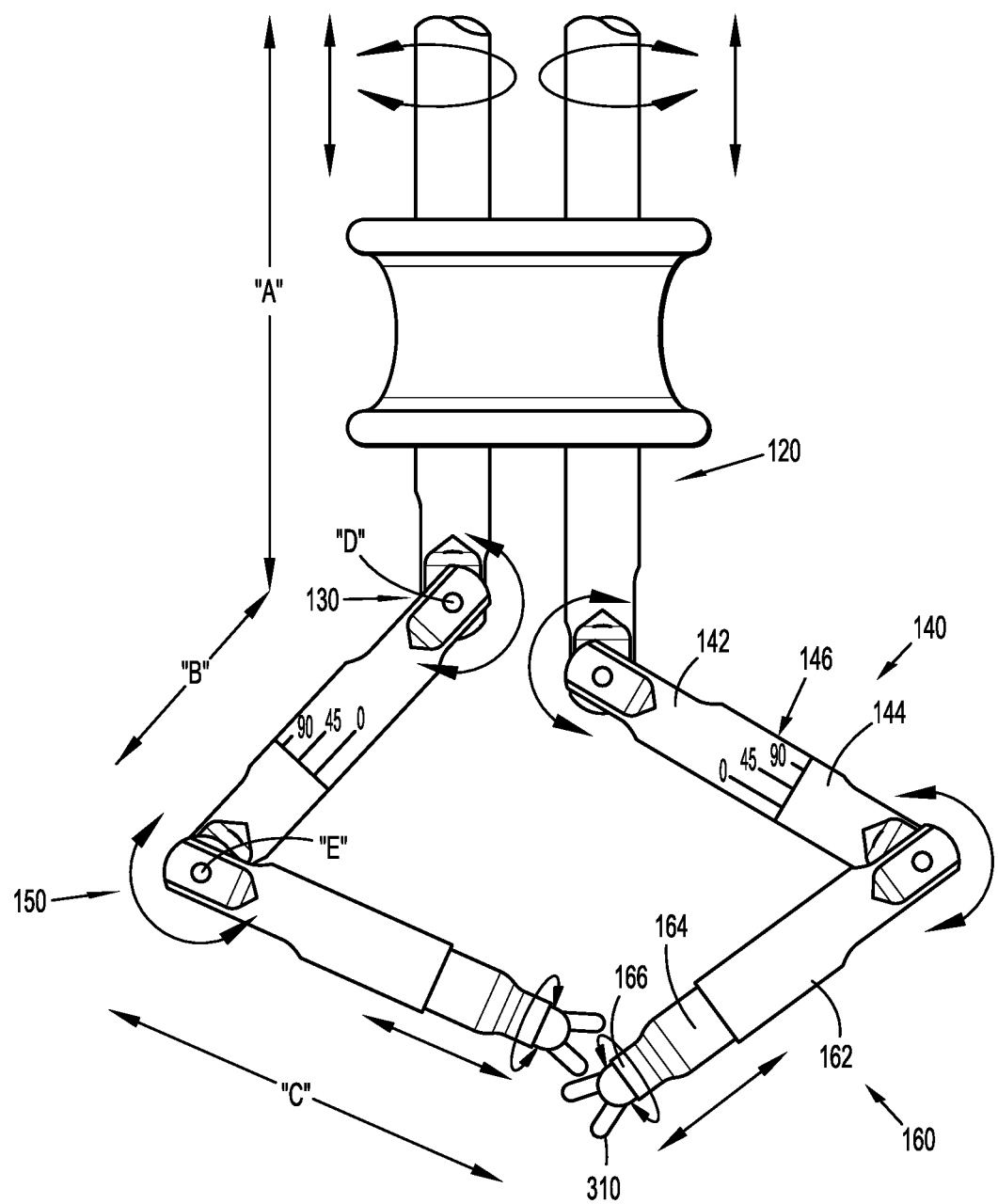
FIG. 2 is a side view of the surgical apparatus of FIG. 1 where joints of the tube members are in a first, parallel configuration.

The middle member 140 includes a first segment 142 and a second segment 144 axially aligned along the axis "B" of the middle member 140. The two segments 142, 144 may be rotatably coupled to each other, resulting in relative rotation therebetween. For instance, the second segment 144 may be configured to rotate relative to the first segment 142 about the axis "B" for a degree from 0° to 360°. The middle member 140 may include a visual indicator 146, as illustrated in FIG. 2, indicating the amount of relative rotation between the two segments 142, 144. The visual indicator 146 includes degree markings, e.g. 0°, 45°, 90°, on the first segment 142, representing 0°, 45°, 90° of rotation of the second segment 144 relative to the first segment 142, respectively. In one embodiment, both the first and second segments 142, 144 of the middle member 140 are hollow segments that allow the surgical object 300 to pass through.

The distal member 160 may also include two segments: a first segment 162 and a second segment 164 that are axially aligned along the axis "C" of the distal member 160. The distal member 160 defines a first, retracted configuration in which the second segment 164 is at least partially retracted within the first segment 162. The distal member 160 also defines a second, extended configuration in which the second segment 164 is fully extended from the first segment 162.

The second segment 164 may be telescopically arranged with respect to the first segment 162 to facilitate retraction and extension of the second segment 164 relative to the first segment 162. For instance, the second segment 164 defines a diameter relatively smaller than that of the first segment 162, such that the second segment 164 may be longitudinally movable relative to the first segment 162 and can slide into the first segment 162. The segment 164 may define a stepped configuration as illustrated in FIG. 1 or a tapered configuration, having a diameter gradually decreasing in the distal direction.

In some embodiments, both the first and second segments 162, 164 of the distal member 160 are hollow segments that allow the surgical object 300 to pass through. The second segment 164 may define a distal opening 166 that allows a distal end or an end effector 310 of the surgical instrument 300 to extend distally beyond the tube member 100. The distal opening 166 is dimensioned to allow the end effector 310 to rotate freely therein as illustrated in FIG. 2. It is also envisioned that the second segment 164 may include a rotation mechanism therein to facilitate rotation of the end effector 310 therein.

In some embodiments, the second segment 164 is passive in nature such that its position is determined by the surgical object 300, particularly by the end effector 310 of the surgical object 300. Longitudinal translation of the end effector 310 through the distal member 160 transits the distal member 160 between the first, retracted configuration and the second, extended configuration. For instance, when inserting the end effector 310 through the tube member 100 in a distal direction, the end effector 310 pushes the second segment 164 out of the first segment 162. On the other hand, when withdrawing the end effector 310 from the tube member 100 in a proximal direction, the end effector 310 retracts the second segment 164 into the first segment 162 by engaging the distal opening 166.

In one embodiment, as illustrated in FIG. 1, the proximal member 120 and the middle member 140 are connected at the first joint 130 which defines an axis "D". The axis "D" is generally perpendicular to the axes "A" and "B" of the proximal member 120 and the middle member 140, respectively. The proximal member 120 and the middle member 140 may rotate or pivot relative to each other about the axis "D," resulting in different angles formed therebetween ranging between approximately 0° and approximately 360°.

In some embodiments, as illustrated in FIG. 1, the first joint 130 includes a first pair of flanges 132, 134 extending distally from the proximal member 120, and a second pair of flanges 136, 138 extending proximally from the middle member 140. The first pair of flanges 132, 134 may be symmetrically arranged about the axis "A" of the proximal member 120 and in parallel relation with the axis "A." Similarly, the second pair of flanges 136, 138 is symmetrically arranged about the axis "B" of the middle member 140 and in parallel relation with the axis "B."

The two pairs of flanges are connected in a manner such that each pair of flanges is rotatable or pivotable relative to the other pair about the axis "D." For instance, the flanges 132, 134, 136, 138 each may define an aperture 139 therethrough, and all apertures 139 are disposed along the axis "D" of the first joint 130. In one embodiment, as illustrated in FIG. 1, the second pair of flanges 136, 138 defines a lateral space therebetween large enough to accommodate the first pair of flanges 132, 134 therein. The first joint 130 may include one pin 133 that securely hold all four flanges by travelling through all four apertures 139, as illustrated in FIGS. 4A-4B. In one embodiment, rotation of the pin 133 effects pivotal motion of the second pair of flanges 136, 138 relative to the first pair of flanges 132, 134 about the axis "D" of the first joint 130, which, in turn, effects pivotal motion of the middle member 140 relative to the proximal member 120 about the first joint 130.

It is envisioned that the first joint 130 may have other configurations that permit relative rotation or pivotal motion between the proximal member 120 and the middle member 140.

The apparatus 10 includes a second joint 150 which jointly connects the middle member 140 to the distal member 160. The second joint 150 defines an axis "E", generally perpendicular to the axes "B" and "C" of the middle member 140 and the distal member 160, respectively. The middle member 140 and the distal member 160 may rotate or pivot relative to each other about the axis "E," resulting in different angles formed therebetween ranging between approximately 0° and approximately 360°.

In one embodiment, the second joint 150 has a similar configuration as that of the first joint 130. For instance, the second joint 150 may include a pair of flanges 152, 154 extending distally from the middle member 140, and another pair of flanges 156, 158 extending proximally from the distal member 160. Each flange defines an aperture 159 therethrough. The second joint may include a pin 153 that travels through all apertures 159 as shown in FIGS. 4A-4B.

The first joint 130 and the second joint 150 may have different arrangements with respect to each other for articulation purposes. For instance, the first and second joints 130, 150 have a first, parallel configuration, as illustrated in FIG. 2, in which their respective axes "D" and "E" are parallel to each other. In this configuration, all three segments 120, 140 and 160 of the tube member 100 all reside in a single plane.

Figure 3:
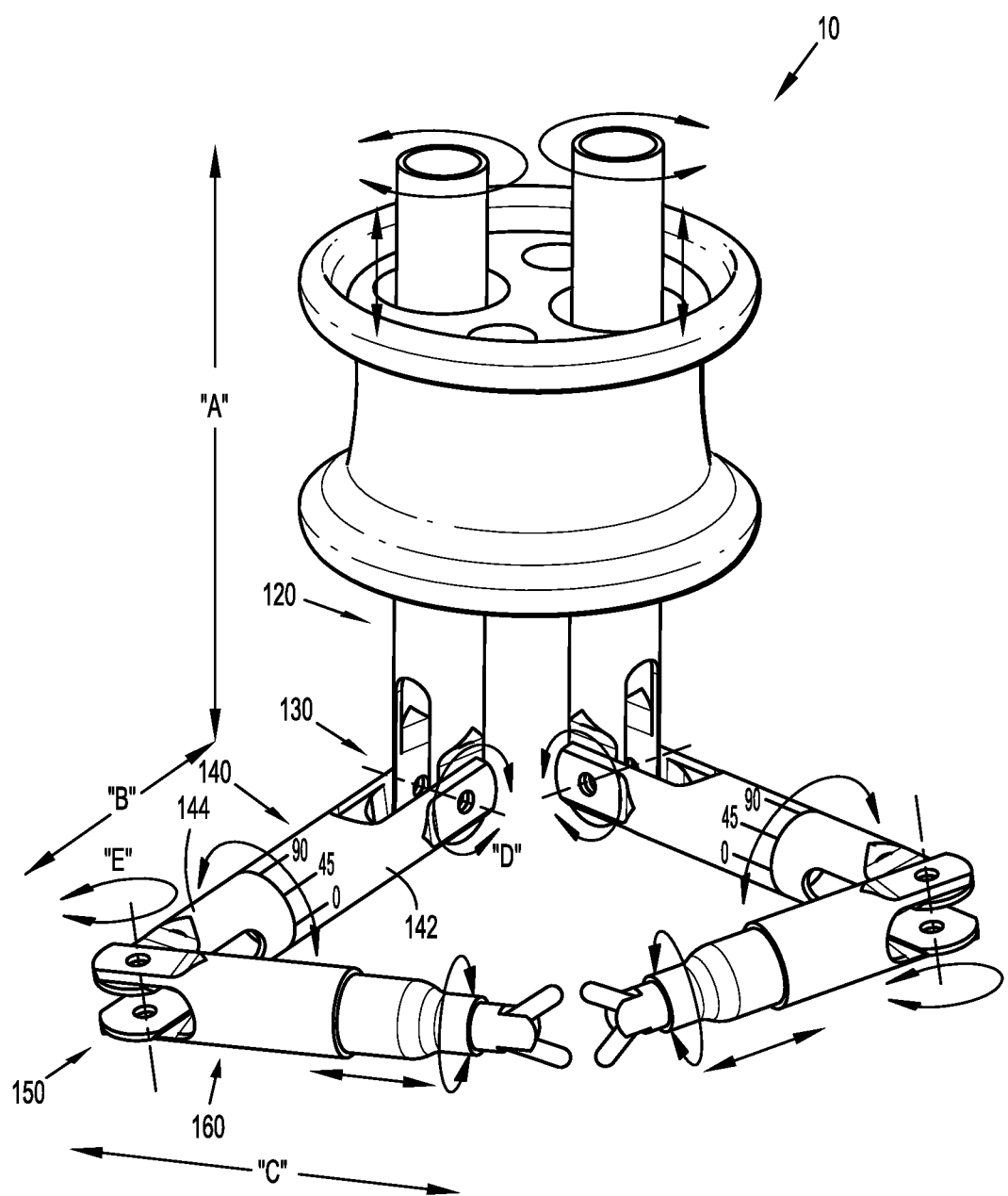
FIG. 3 is a front perspective view of the surgical apparatus of FIG. 1 where joints of the tube members are in a second, perpendicular configuration.

The two joints 130, 150 may also have a second, perpendicular configuration, as illustrated in FIG. 3, in which their respective axes "D" and "E" are generally perpendicular with respect to each other. In this configuration, the middle member 140 and the distal member 160 may reside in a single plane, which is generally perpendicular to the proximal member 120.

The first and second joints 130, 150 may define other configurations in which their respective axes "D" and "E" define angles of different degrees therebetween.

It is envisioned that relative rotation between the two segments 142 and 144 of the middle member 140 adjusts the angle defined between the axes "D" and "E," which, in turn, transits the first and second joints 130, 150 to different arrangements with respect to each other.

In one embodiment, the first segment 142 and the second segment 144 of the middle member 140 are fused together, or permanently attached to each other by other mechanisms, as one single, integral piece, such that no relative rotation is allowed therebetween. In this embodiment, the first and second joints 130, 150 are designated and confined to a particular configuration, e.g., the first, parallel configuration or the second, perpendicular configuration.

In another embodiment, the first segment 142 and the second segment 144 of the middle member 140 are rotatably coupled to each other, selectively preset to a particular degree of rotation therebetween before the introduction of the tube member 100 into the body cavity, and configured to maintain that particular degree of rotation after introduction of the tube member 100 into the body cavity. In this embodiment, the first and second joints 130, 150 are selectively preset to a particular configuration, e.g., the first, parallel configuration or the second, perpendicular configuration, and the two joints 130, 150 are confined to the particular configuration when positioned within the body cavity, and can be reset to another configuration after being removed from the body cavity.

In yet another embodiment, the first segment 142 and the second segment 144 of the middle member 140 are rotatably coupled to each other, and are selectively adjustable to different degrees of rotation both before and after the tube member 100 is positioned into the body cavity. For instance, after the tube member 100 is inserted into the body cavity, the two joints 130, 150 may be adjusted to a plurality of configurations, including the first, parallel configuration and the second, perpendicular configuration, with different angular orientations to facilitate the surgical object 300 to access different areas in the body cavity.

Additionally, the apparatus 10 includes an articulation mechanism to effect articulation of the tube member 100.

In one embodiment, as illustrated in FIGS. 4A-4B, the apparatus 40 includes at least one cable to articulate the tube member 100. The apparatus 40 may include a first cable 430 configured to rotate the first joint 130 as illustrated in FIG. 4A. The first cable 430 extends along the length of the proximal member 120, and has a distal end 432 extending distally beyond the proximal member 120. The distal end 432 may be connected to an inner wall of the middle member 140. Specifically, the distal end 432 of the first cable 430 may be permanently connected to an inner wall of the first segment 142 of the middle member 140 by gluing, fusing or an over-molding process. The first cable 430 has a proximal end extending proximally beyond the proximal member 120 to be manipulated by the user. It is envisioned that pulling the first cable 430 in a proximal direction lifts the middle member 140 proximally, which induces rotation of the first joint 130 in a first rotational direction, e.g. clockwise direction, and simultaneously causes pivotal motion of the middle member 140 relative to the proximal member 120 about the first joint 130 in a first pivotal direction. Upon release of the pulling force from the first cable 430, the middle member 140 would tend to resume its linear position axially aligned with respect to the proximal member 120 due to gravity, causing the first joint 130 to rotate in a second rotational direction opposite to the first rotation, e.g., counterclockwise direction.

The apparatus 40 may also include a second cable 450 configured to rotate the second joint 150 as illustrated in FIG. 4B. The second cable 450 extends along the length of the proximal member 120 and the middle member 140. The second cable 450 has a distal end 452 connected to one of the flanges 156, 158 extending proximally from the distal member 160. For instance, the distal end 452 may be permanently connected to an inner wall of the flange 158 by gluing, fusing or an over-molding process. The second cable 450 has a proximal end that extends proximally beyond the proximal member 120 to be manipulated by the user. Similar to the behavior of the first cable 430 described above, pulling the second cable 450 rotates the second joint 150 and pivots the distal member 160 relative to the middle member 140 about the second joint 150.

As illustrated in FIGS. 4A-4B, when the first and second joints 130, 150 are in the first, parallel configuration, pulling the first cable 430 and pulling the second cable 450 facilitate the tube member 100 to reach different positions in the single plane. The first and second cables 430, 450 may comprise a semi-rigid, flexible material that conforms to different configurations of the tube member 100.

There are different arrangements of the first and second cables 430, 450 relative to the tube member 100 as illustrated in FIGS. 5A-5B. For instance, the two cables 430, 450 may be disposed within the tube member 100 as illustrated in FIG. 5A. Specifically, the inner wall 111 of the tube member 100 may define two small openings 112, 114 positioned circumferentially in the inner wall 111, and each opening 112, 114 is configured to accommodate one of the cables 430, 450. Alternatively, as illustrated in FIG. 5B, the two cables 430, 450 may be disposed outside of the tube member 100, and positioned circumferentially about the tube member 100.

In an alternate embodiment, as illustrated in FIG. 6, the apparatus 60 may include a rigid arm 610 and a sleeve 620 to articulate the tube member 100. The rigid arm 610 is configured to articulate the tube member 100 by specifically adjusting the position of the distal member 160 of the tube member 100 via the sleeve 620.

The rigid arm 610 is disposed along the length of the tube member 100, and has a proximal end extending proximally beyond the proximal member 120 of the tube member 100. The rigid arm 610 has a distal end 612 attached to the sleeve 620. The distal end 612 may be attached to the sleeve 620 in a manner which allows relative pivotal motion between the rigid arm 610 and the sleeve 620.

The sleeve 620 has an annular configuration and defines a lumen 622 therethrough dimensioned to accommodate the distal member 160 of the tube member 100 therein. In some embodiments, the sleeve 620 is configured to slide at least partially along the axis "C" of the distal member 160. In one embodiment, the sleeve 620 is dimensioned to be circumferentially, frictionally engaged with the first segment 162 of the distal member 160. In another embodiment, the sleeve 620 is dimensioned to be loosely coupled to the distal member 160 so that the sleeve 620 may rotate relative to the distal member 160.

In operation, as seen in FIG. 6, pulling the rigid arm 610 moves the distal member 160 longitudinally via the sleeve 620. As the proximal member 120 remains stationary, longitudinal motion of the distal member 160 translates into pivotal motion of the distal member 160 relative to the middle member 140, as well as pivotal motion of the middle member 140 relative to the proximal member 120.

Optionally, the apparatus 60 may also include a cable 630 in conjunction with the rigid arm 610 and the sleeve 620 to articulate the tube member 100. The cable 630 extends along the longitudinal length of the tube member 100, with a distal end 632 connected to the distal member 160, and a proximal end extending proximally beyond the proximal member 120. The cable 630 may comprise a semi-rigid, flexible material. In one embodiment, the cable 630 is disposed within the tube member 100, as illustrated in FIG. 6, while the rigid arm 610 is disposed outside of the tube member 100. Alternatively, the cable 630 may be disposed outside of the tube member 100, as illustrated in FIG. 7, while the rigid arm 610 is partially disposed within the tube member 100.

The cable 630 is configured to assist the rigid arm 610 and the sleeve 620 in articulating the tube member 100. For instance, pulling or pushing the cable 630 effects longitudinal motion of the distal member 160, causing pivotal motion of the distal member 160 relative to the middle member 140, which, in turn, causes pivotal motion of the middle member 140 relative to the proximal member 120.

There are different arrangements of the rigid member 610 relative to the tube member 100. For instance, as illustrated in FIG. 6, the rigid member 610 may be disposed outside of and in parallel relation with the tube member 100.

In another embodiment of the surgical apparatus 70, as illustrated in FIG. 7, the rigid member 610 may be partially disposed within the tube member 100 and partially disposed outside of the tube member 100. In particular, the rigid member 610 has a first portion 616 disposed within the proximal member 120 of the tube member 100, and has a second portion 618 extending distally beyond the proximal member 120. Also, as illustrated in FIG. 7, the distal end 612 of the rigid arm 610 is hingedly attached to the sleeve 620 via a hinge connection 614. The hinge connection 614 between the rigid arm 610 and the sleeve 620 allows relative pivotal motion between the rigid arm 610 and the sleeve 620.

Figure 8:
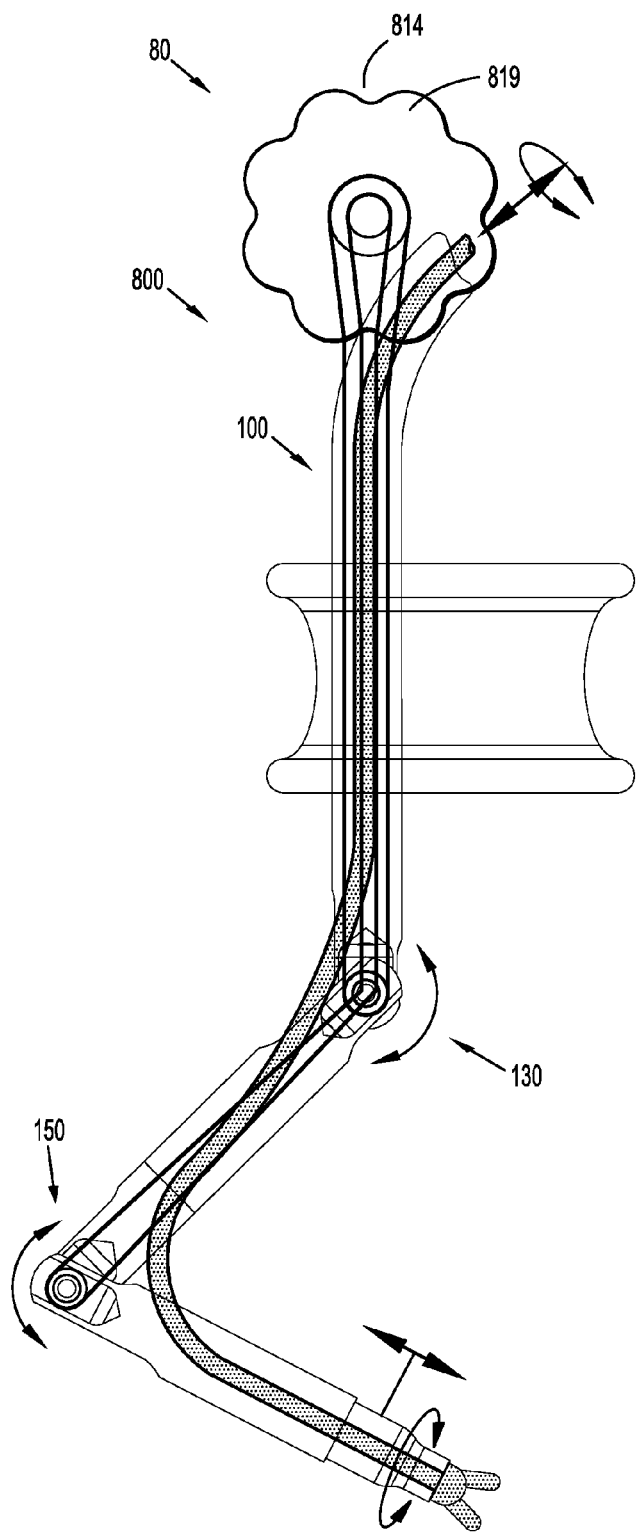
FIG. 8 illustrates yet another embodiment of the surgical apparatus of FIG. 1 including a closed-loop system.
Figure 9:
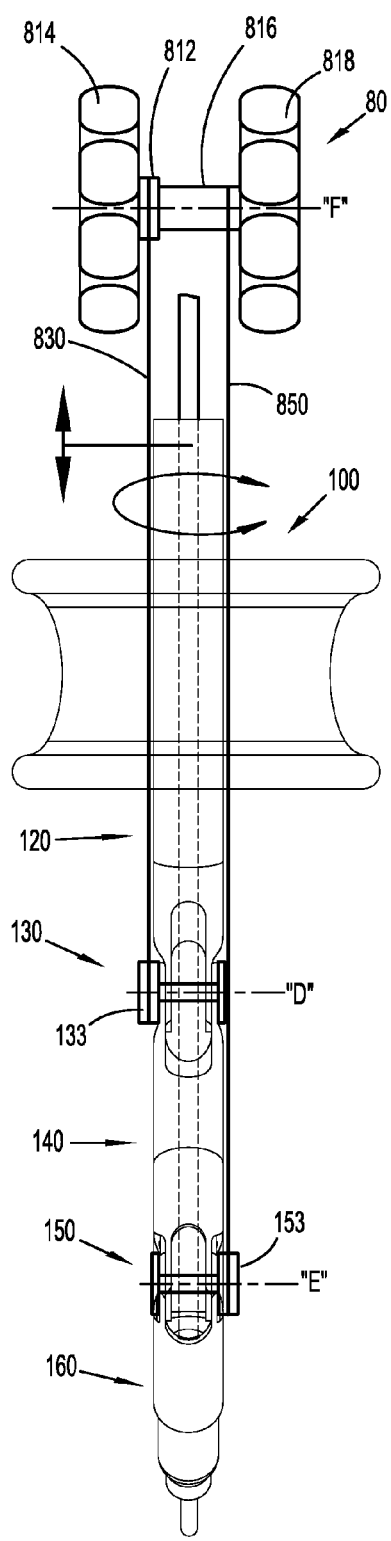
FIG. 9 is a side view of the surgical apparatus of FIG. 8.

In another embodiment, as illustrated in FIGS. 8-9, the apparatus 80 includes a closed-loop cable-wheel system 800 to articulate the tube member 100. The closed-loop cable-wheel system 800 includes a first rotatable member 812, which may exhibit a cylindrical configuration or other configurations. The first rotatable member 812 is configured to rotate about an axis "F."

Figure 10:
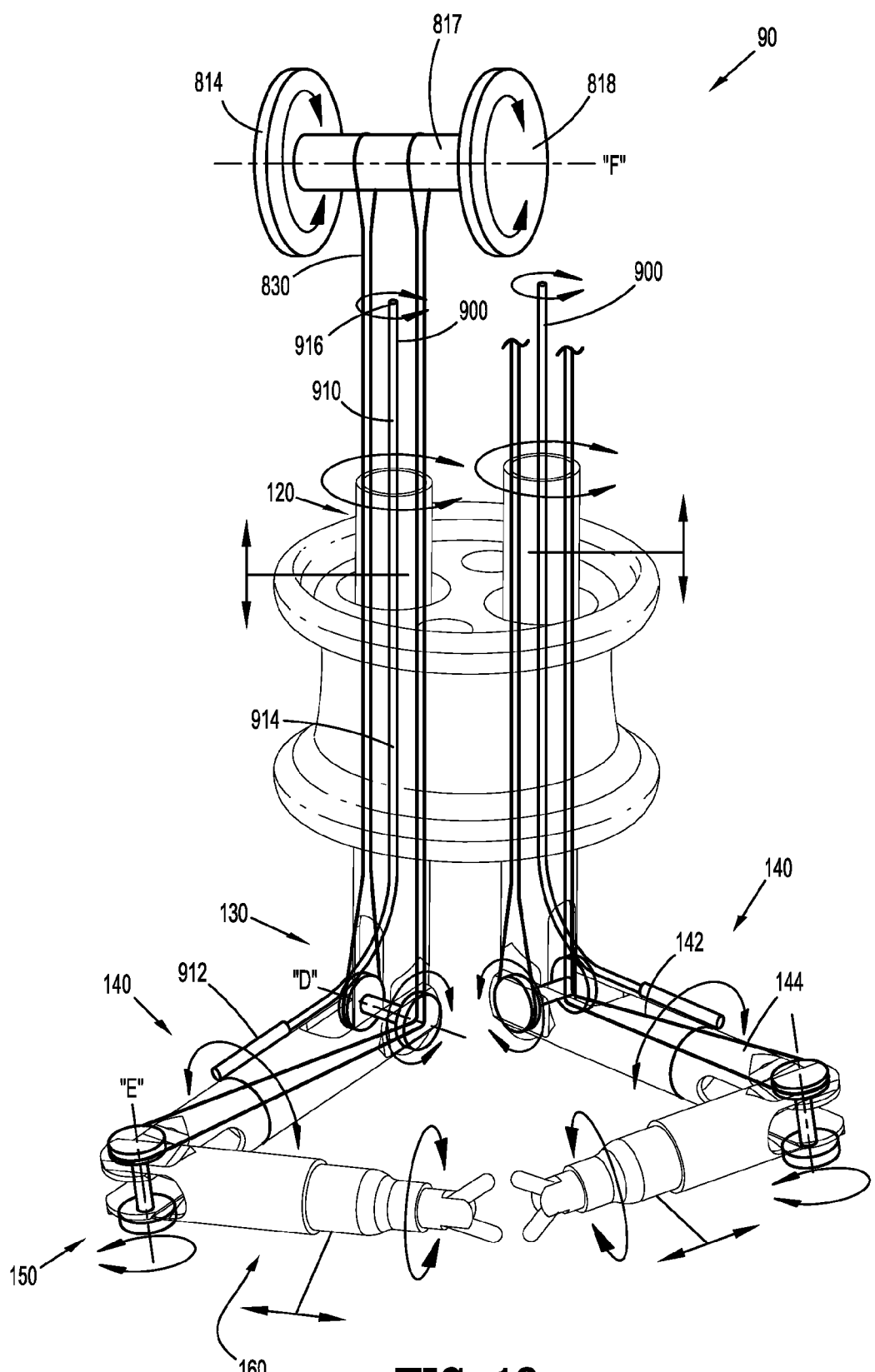
FIG. 10 illustrates another embodiment of the surgical apparatus of FIG. 1.

It is envisioned that when the first joint 130 and the second joint 150 are in the first, parallel configuration as illustrated in FIGS. 8-9, the axis "F" is parallel to axes "D" and "E" of the first joint 130 and the second joint 150, respectively. On the other hand, when the first joint 130 and the second joint 150 are in the second, perpendicular configuration as illustrated in FIG. 10, the axis "F" may be parallel to the axis "D" of the first joint 130, and perpendicular to the axis "E" of the second joint 150.

As shown in FIG. 9, the first rotatable member 812 has a first knob 814 attached thereto, such that rotation of the first knob 814 about the axis "F" effects rotation of the first rotatable member 812. The first rotatable member 812 may be permanently attached to the first knob 814 or releasably connected to the first knob 814.

The first knob 814 may have an uneven outer circumference defining a plurality of protrusions 819 around its circumference, as illustrated in FIGS. 8-9, to facilitate frictional engagement between fingers and the first knob 814 during manual manipulation. Alternatively, the first knob 814 may define an even outer circumference, e.g. a circular configuration, as illustrated in FIG. 10.

The system 800 includes a first cable 830 that loops about the first rotatable member 812 and the first joint 130, e.g., the pin 133 of the first joint 130, resulting in a first loop formed therebetween. In one embodiment, the first cable 830 is disposed outside of the tube member 100 as illustrated in FIG. 9. Alternatively, the first cable 830 is disposed partially within the tube member 100, e.g., within the proximal member 120 of the tube member 100, as illustrated in FIG. 10.

In operation, rotation of the first knob 814 effects rotation of the first rotatable member 812 which, in turn, causes rotation of the pin 133 of the first joint 130 via the first cable 830. Rotation of the pin 133 causes pivotal motion of the middle member 140 relative to the proximal member 120.

The system 800 may include a second loop that effects rotation of the second joint 150, in a manner similar to the first loop. Specifically, as illustrated in FIG. 9, the system 800 includes a second rotatable member 816 concentrically formed with respect to the first rotatable member 812, and has a second knob 818 attached to the second rotatable member 816. A second cable 850 loops about the second rotatable member 816 and the second joint 150, e.g., the pin 153 of the second joint 150, resulting in a second loop.

Rotation of the second knob 818 effects rotation of the second rotatable member 816, which, in turn, causes rotation of the pin 153 of the second joint 150 via the second cable 850. Rotation of the pin 153 causes pivotal motion of the distal member 160 relative to the middle member 140.

In one embodiment, the first and second rotatable members 812, 816 are configured to rotate independent of each other, so that rotation of the first and second joints 130, 150 are independent of each other.

In another embodiment, the first rotatable member 812 and the second rotatable member 816 are monolithically formed into a single rotatable member 817 as illustrated in FIG. 10. Rotation of any one of the first and second knobs 814, 818 causes synchronous rotation of the other knob, which, in turn, results in synchronous rotations of the first joint 130 and the second joint 150. Accordingly, rotation of any one of the knobs 814, 818 causes pivotal motion of the middle member 140 relative to the proximal member 120, and simultaneously causes pivotal motion of the distal member 160 relative to the middle member 140.

In yet another embodiment, the apparatus 90 may include a rotation system 900, illustrated in FIG. 10, which effects relative rotation between the first and second segments 142, 144 of the middle member 140, when the first and second segments 142, 144 are rotatably coupled to each other.

As illustrated in FIG. 10, the rotation system 900 includes a cable 910 that is disposed within the proximal member 120 and extends along the length thereof. The cable 910 has a distal end 912 extending distally beyond the proximal member 120 and connected to one of the two segments 142, 144 of the middle member 140. For instance, as illustrated in FIG. 10, the distal end 912 may extend along the length of the first segment 142, and is attached to an outer surface of the second segment 144. It is envisioned that the cable 910 may be permanently attached to the second segment 144 by gluing, welding or an over-molding process.

The cable 910 may have a proximal end 916 extending proximally beyond the proximal member 120 and operatively connected to a torque shaft (not shown). It is envisioned that rotation of the torque shaft effects rotation of the cable 910, which, in turn, effects rotation of the second segment 144 of the middle member 140 while the first segment 142 and the proximal member 120 remain stationary.

Figure 11:
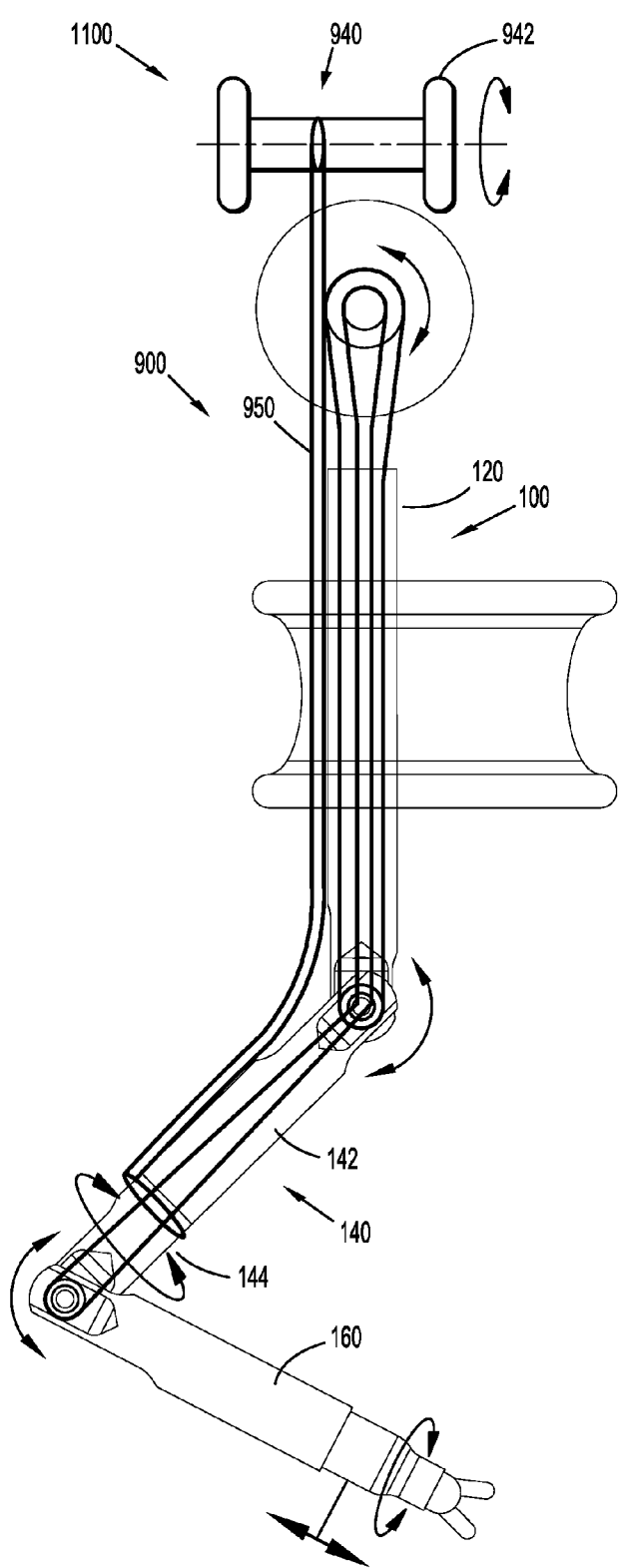
FIG. 11 illustrates yet another embodiment of the surgical apparatus of FIG. 1.

In another embodiment of the surgical apparatus 1100, as illustrated in FIG. 11, the rotation system 900 may implement a rotate-to-rotate mechanism to effect rotation of the second segment 144 of the middle member 140 relative to the first segment 142 thereof. For instance, the rotation system 900 includes a rotatable member 940 with a pair of knobs 942 disposed proximally beyond the proximal member 120. The rotation system 900 further includes a cable 950 that loops about the rotatable member 940 and the second segment 144 of the middle member 140, forming a loop therebetween. The cable 950 is disposed about the second segment 144 in a manner such that rotation of the rotatable member 940 effects rotation of the second segment 144 relative to the first segment 142, via the cable 950. The cable 950 may be disposed outside of the tube member 100 and loop exteriorly around the second segment 144 as illustrated in FIG. 11. Alternatively, the cable 950 may be disposed within the tube member 100 and loop interiorly around the second segment 144.

Figure 12:
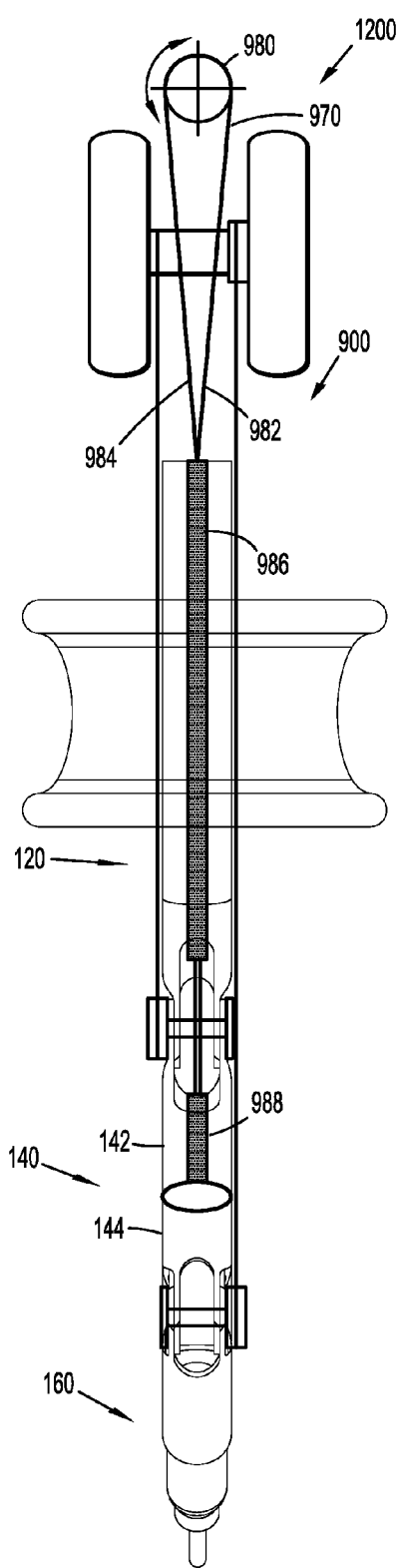
FIG. 12 illustrates another alternate embodiment of the surgical apparatus of FIG. 1.

In another alternate embodiment of the surgical apparatus 1200 as illustrated in FIG. 12, the rotation system 900 may implement a pull-pull-to-rotate mechanism to effect rotation of the second segment 144 of the middle member 140 relative to the first segment 142 thereof. For instance, as illustrated in FIG. 12, the rotation system 900 includes a support member 980 disposed proximally beyond the proximal member 120. The rotation system 900 further includes a cable 970 that loops around the second segment 144 of the middle member 140 and the support member 980. The cable 970 may be disposed inside of the tube member 100 and loop interiorly around the second segment 144 of the middle member 140. For instance, as shown in FIG. 12, the cable 970 has a first portion 982 and a second portion 984, in parallel relationship with each other. Both portions 982, 984 are disposed within the proximal member 120 and the first segment 142 of the middle member 140, and extend along the length of the proximal member 120 and the first segment 142 of the middle member 140.

The rotation system 900 may include a first sleeve 986 disposed interiorly within the proximal member 120 along the length thereof, and a second sleeve 988 disposed interiorly within the first segment 142 along the length thereof. The two sleeves 986, 988 are axially aligned and dimensioned to accommodate the two parallel portions 982, 984 of the cable 970.

It is envisioned pulling the first portion 982 rotates the second segment 144 of the middle member 140 in one direction, e.g. clockwise rotation, and pulling the second portion 984 rotates the second segment 144 of the middle member 140 in an opposite direction, e.g. counterclockwise rotation.

Alternatively, the sleeves 986, 988 and the cable 970 may be disposed outside of the tube member 100. The cable 970 may loops exteriorly around the second segment 144 of the middle member 140.

The above disclosure provides different embodiments of the apparatus 10 and different mechanisms to actuate the apparatus 10. In operation, the user first insufflates the body cavity of a patient through an opening, e.g., the navel of the patient, and then positions an anchor member 200 within the opening. Next, the user advances a tube member 100 through the anchor member 200 until the proximal member 120 of the tube member 100 sealingly engages the anchor member 200. The user then inserts a surgical object 300 through the tube member 100 until the end effector 310 of the surgical object 300 reaches distally beyond the tube member 100. Alternatively, the user may insert the surgical object 300 into the tube member 100, and advance the tube member 100 with the surgical object 300 mounted therein into the anchor member 200. After the end effector 310 of the surgical object 300 enters the body cavity, the user can selectively adjust the position of the end effector 310 by articulating the tube member 100.

The surgical apparatus 10 and method of its operation as disclosed herein presents many significant advantages over the prior art and provides significant benefits to the surgeon during surgical procedures. First, the surgical apparatus 10 by implementing articulation mechanisms removes articulation mechanisms that are otherwise implemented on the surgical object 300, simplifying the surgical object 300, and reducing design and manufacture costs of the surgical object 300. Further, the surgical apparatus 10 provides the surgical object 300 inserted therein three-dimensional freedom of movement, and gives the surgical object 300 a better angular access to the target surgical site, benefiting a wide variety of surgical procedures. Additionally, the hollow design of the surgical apparatus 10 facilitates easy insertion and removal of the surgical object 300 therethrough. The telescopic configuration of the distal member 160 of the tube member 100 stabilizes and facilitates control of the end effector 310. Further, the overall design and configuration of the surgical apparatus 10 allows it to be reused with multiple disposable anchor members, therefore reducing the overall cost of minimally invasive surgical procedures.

While several embodiments of the disclosure have been shown in the drawings and/or discussed herein, it is not intended that the disclosure be limited thereto, as it is intended that the disclosure be as broad in scope as the art will allow and that the specification be read likewise.

Therefore, the above description should not be construed as limiting, but merely as exemplifications of particular embodiments. Different embodiments of the disclosure may be combined with one another based on the particular needs of the surgical procedures. Those skilled in the art will envision other modifications within the scope and spirit of the claims appended hereto.

What is claimed is:

1. A method of articulating a flexible surgical object positioned within a tissue tract accessing an underlying body cavity, comprising:
   positioning a surgical apparatus within the tissue tract, the surgical apparatus comprising
      a tube member defining a longitudinal axis and a lumen therethrough, the lumen adapted to receive the flexible surgical object therein, the tube member including:
      a proximal member;
      a middle member pivotably connected to the proximal member at a first joint, the middle member including a first segment and a second segment, the first and second segments disposed coaxially along the middle member and configured to rotate relative to each other about a common axis; and
      a distal member pivotably connected to the middle member at a second joint, the distal member including a third segment and a fourth segment, the third segment and the fourth segment disposed coaxially along the distal member, the fourth segment configured to extend from and retract within the third segment;
   inserting the tube member into an access device, which is configured to be positioned within the tissue tract for providing access to the underlying body cavity;
   inserting the flexible surgical object into the tube member; and
   articulating the tube member to articulate the flexible surgical object.

2. The method of articulating the flexible surgical object according to claim 1, wherein positioning the surgical apparatus includes the surgical apparatus having at least one cable associated with at least one of the first and second joints in a manner such that pulling the at least one cable rotates the associated joint.

3. The method of articulating the flexible surgical object according to claim 1, wherein positioning the surgical apparatus includes the surgical apparatus having a rigid arm extending along the tube member, and a sleeve mounted about the distal member, the rigid arm and the sleeve being hingedly connected to each other.

4. The method of articulating the flexible surgical object according to claim 3 including pulling the rigid arm to articulate the middle member and the distal member relative to the proximal member.

5. The method of articulating the flexible surgical object according to claim 1, wherein positioning the surgical apparatus includes the surgical apparatus having a closed-loop system which effects rotation of at least one of the first and second joints.

6. The method of articulating the flexible surgical object according to claim 1, wherein positioning the surgical apparatus includes the surgical apparatus having a rotation system which effects relative rotation between a first segment and a second segment that are disposed axially along the middle member.

7. The method of articulating the flexible surgical object according to claim 1, wherein articulating the tube member includes positioning the first joint and the second joint in a parallel configuration.

8. The method of articulating the flexible surgical object according to claim 7, wherein articulating the tube member includes positioning the first joint and the second joint in a perpendicular configuration.

9. The method of articulating the flexible surgical object according to claim 8, wherein articulating the tube member includes rotating the first segment and the second segment of the middle member to transition the first joint and the second joint from the parallel configuration to the perpendicular configuration.

10. The method of articulating the flexible surgical object according to claim 1, further including rotating an end effector of the flexible surgical object within the distal member.

* * * * *